US012385799B2

United States Patent
Aceto et al.

(10) Patent No.: US 12,385,799 B2
(45) Date of Patent: *Aug. 12, 2025

(54) APPARATUSES AND METHODS FOR DETECTING LEAKS IN A NEGATIVE PRESSURE WOUND THERAPY SYSTEM

(71) Applicant: Smith & Nephew, Inc., Memphis, TN (US)

(72) Inventors: Paul Aceto, Providence, RI (US); Kealoha Young Deutch, Odessa, FL (US); Joseph Gordon, Mansfield, MA (US); Luke Hagan, Seattle, WA (US); William Joseph Jaecklein, Saint Petersburg, FL (US); Bill Kane, Sutton, MA (US); Dino Kasvikis, Mansfield, MA (US); Corey Libby, Sutton, MA (US); Jacob A. Marks, Providence, RI (US); Michael Salame, Providence, RI (US); Jared Schneider, Cranston, RI (US)

(73) Assignee: Smith & Nephew, Inc., Memphis, TN (US)

(*) Notice: Subject to any disclaimer, the term of this patent is extended or adjusted under 35 U.S.C. 154(b) by 200 days.

This patent is subject to a terminal disclaimer.

(21) Appl. No.: 17/977,765

(22) Filed: Oct. 31, 2022

(65) Prior Publication Data
US 2023/0103577 A1 Apr. 6, 2023

Related U.S. Application Data

(63) Continuation of application No. 16/400,965, filed on May 1, 2019, now Pat. No. 11,484,638, which is a
(Continued)

(51) Int. Cl.
*G01M 3/24* (2006.01)
*A61M 1/00* (2006.01)

(52) U.S. Cl.
CPC ............... *G01M 3/24* (2013.01); *A61M 1/73* (2021.05); *A61M 1/912* (2021.05); *A61M 1/913* (2021.05);
(Continued)

(58) Field of Classification Search
CPC ............... G01M 3/24; A61M 2205/15; A61M 2205/18; A61M 1/73; A61M 1/913; A61M 1/916; A61M 1/912
(Continued)

(56) References Cited

U.S. PATENT DOCUMENTS 7,625,362 B2 12/2009 Boehringer et al.
7,700,819 B2 4/2010 Ambrosio et al.
(Continued)

FOREIGN PATENT DOCUMENTS

EP 3216481 A1 9/2017
WO WO-2009151645 A2 12/2009
(Continued)

OTHER PUBLICATIONS

International Preliminary Report on Patentability for Application No. PCT/US2012/062307, mailed on May 15, 2014, 6 pages.
(Continued)

*Primary Examiner* — Andrew J Mensh
(74) *Attorney, Agent, or Firm* — Knobbe, Martens, Olson & Bear, LLP (57) ABSTRACT

Leak location devices and methods of using leak location devices that can be used in conjunction with negative pressure wound therapy systems are disclosed. In some embodiments, a leak location device can include a microphone for detecting sound pressure produced by a leak. Detected sound pressure can be compared to a threshold, which can correspond to background or ambient sound pressure. Background or ambient sound pressure can corre-
(Continued)

spond to sound produced by a negative pressure source. The leak detection device can include a display configured to visually depict the detected sound, and a light source which creates a visual depiction of the coverage angle of the microphone.

10 Claims, 11 Drawing Sheets

Related U.S. Application Data continuation of application No. 15/472,672, filed on Mar. 29, 2017, now Pat. No. 10,307,516, which is a continuation of application No. 14/354,916, filed as application No. PCT/US2012/062307 on Oct. 26, 2012, now Pat. No. 9,610,388.

(60) Provisional application No. 61/553,858, filed on Oct. 31, 2011.

(52) U.S. Cl.
CPC ......... *A61M 1/916* (2021.05); *A61M 2205/15* (2013.01); *A61M 2205/18* (2013.01)

(58) Field of Classification Search
USPC ........................................................ 604/318
See application file for complete search history.

(56) References Cited

U.S. PATENT DOCUMENTS

| | | |
|---|---|---|
| 7,779,625 B2 | 8/2010 | Joshi et al. |
| 8,061,360 B2 | 11/2011 | Locke et al. |
| 8,062,272 B2 | 11/2011 | Weston |
| 8,097,272 B2 | 1/2012 | Addison |
| 8,500,718 B2 | 8/2013 | Locke et al. |
| 9,610,388 B2 | 4/2017 | Aceto et al. |
| 10,307,516 B2 | 6/2019 | Aceto et al. |
| 2007/0016152 A1 | 1/2007 | Karpowicz et al. |
| 2009/0177051 A1* | 7/2009 | Arons ................ A61B 5/0059 |
| | | 128/898 |
| 2010/0207768 A1* | 8/2010 | Pidgeon ................ A61M 1/784 |
| | | 340/573.1 |
| 2011/0190735 A1* | 8/2011 | Locke .................. F04B 45/047 |
| | | 604/543 |
| 2011/0245682 A1* | 10/2011 | Robinson .............. G01M 3/002 |
| | | 600/473 |
| 2012/0035561 A1 | 2/2012 | Locke et al. |
| 2013/0066285 A1 | 3/2013 | Locke et al. |

FOREIGN PATENT DOCUMENTS

| | | |
|---|---|---|
| WO | WO-2012028842 A1 | 3/2012 |
| WO | WO-2013039622 A2 | 3/2013 |

OTHER PUBLICATIONS

International Search Report and Written Opinion for Application No. PCT/US2012/062307, mailed on Mar. 7, 2013, 10 pages.

* cited by examiner

APPARATUSES AND METHODS FOR DETECTING LEAKS IN A NEGATIVE PRESSURE WOUND THERAPY SYSTEM

This application is a continuation of U.S. patent application Ser. No. 16/400,965, filed May 1, 2019, which is a continuation of U.S. patent application Ser. No. 15/472,672, filed Mar. 29, 2017, now U.S. Pat. No. 10,307,516, which is a continuation of U.S. patent application Ser. No. 14/354,916, filed Apr. 28, 2014, now U.S. Pat. No. 9,610,388, which is a national stage application of International Patent Application No. PCT/US2012/062307, filed on Oct. 26, 2012, which claims priority to U.S. Provisional Patent Application No. 61/553,858, filed Oct. 31, 2011. The disclosure of each of these prior applications is hereby incorporated by reference in its entirety.

BACKGROUND

Field of the Disclosure

Embodiments of the present invention relate generally to the treatment of wounds using negative pressure wound therapy systems, and more specifically to improved apparatuses and methods for detecting leaks in such systems.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover.

There are numerous interfaces in the negative pressure wound therapy systems currently known in the art, for attaching the cover as well for connecting the source of negative pressure to the cover. One example is an adhesive interface. Leaks can occur at these interfaces, for example, because of creases or apertures in the surface of the cover or because of creases in the tissue of the patient. Leaks may reduce the effectiveness of therapy provided by the negative pressure wound therapy system. Leaks can be difficult to locate and reduce.

SUMMARY OF THE DISCLOSURE

Embodiments of the invention disclosed herein are directed to leak location apparatuses and methods of using a leak location device, and can be used in conjunction with negative pressure wound therapy systems.

Certain embodiments of the invention employ a monitoring device for locating leaks. In some embodiments, a leak detection device, such as an acoustic monitoring device, can be used for detecting the sound produced by a leak. For example and for illustrative purposes only, some embodiments can employ a sound level meter comprising a directional microphone for detecting the sound waves produced by the leak. Using a directional microphone can be effective at locating leaks due to the microphone having a coverage angle which picks up sound waves from a specific location, thereby limiting background or ambient noise sources or interferences. For example, a negative pressure pump can be configured to provide −80 mmHg of reduced pressure and background or ambient noise sources, which include the pump, can be measured at 10 dBA or higher. The coverage angle, which can also be referred to as the pickup arc, coverage area, cone, or microphone aperture, refers to the area from which the microphone receives sound waves. Certain embodiments employ a microphone constructed to allow a narrow and predominantly forward discrimination to facilitate locating and isolating leaks. In some embodiments, a leak detection device comprising a unidirectional microphone or microphone arrays can be used. Some embodiments can comprise an indicator device (e.g., display) configured to visually or otherwise depict the detected sound, and a light source which creates a visual depiction of the coverage angle of the microphone. In some embodiments, a light emitting diode (LED), laser, etc., or any combination thereof can be employed to create the visual indicator of the coverage angle.

Certain embodiments provide for leak detection in a negative pressure wound therapy system comprising a wound packing material configured to be positioned in the wound cavity or on the wound surface, a cover or drape (e.g., flexible drape) configured to be positioned over the wound packing material and sealed to the tissue surrounding the wound, a source of negative pressure, and a conduit or plurality of conduits configured to transmit negative pressure to the wound. The system can further comprise a leak detection device (e.g., an acoustic monitoring device). In some embodiments, the system can include a collection canister connected to the source of negative pressure and configured to collect fluid and/or exudate aspirated or removed from the wound. In some embodiments, the negative pressure may be delivered through a bridge interface.

Some embodiments can further comprise a suction adapter comprising at least two layers constructed from a substantially fluid impermeable material and an adhesive layer on the wound-facing surface of the bottom layer, an aperture in the bottom layer in fluid communication with the wound site through the opening, a conduit connected between the source of negative pressure and the suction adapter, the conduit further positioned between the layers of the suction adapter and passing through the aperture in the bottom layer into the opening in the flexible drape. Certain other embodiments can further comprise a port integrated into the drape with an adhesive layer on the wound-facing surface of the drape.

In some embodiments, a wound dressing can be placed over the wound and create a substantially fluid impermeable seal. A negative pressure source (e.g., pump) can be connected to the dressing to establish and maintain reduced pressure under the dressing. The negative pressure source can be configured to detect and/or provide indication of leaks (e.g., leaks in the seal) in the system. A leak detection device can be used to identify the location of the leak. In certain embodiments, the leak detection device may further comprise a display configured to visually depict the sound waves detected by a microphone and a light source which creates a visual depiction of the coverage angle of the microphone.

In some embodiments, the leak detection device can comprise a separate detection device (e.g., a hand held detection device) configured to be in wireless or wired communication with an indicator device (e.g., display). In some embodiments, a leak detection device can use a microphone to detect the sound produced by a leak or leaks. The leak detection device can be configured to indicate the location of the leak. In some embodiments, the leak detection device may further comprise a display configured to visually depict the sound waves received by the microphone. In some embodiments, the leak detection device can be a portable electronic device (e.g., a smart phone comprising a microphone) and a sound visualization software application. In some embodiments, the leak detection device can comprise a directional microphone and a device which creates a visual depiction of the coverage angle of the microphone. In some embodiments, the device depicting the coverage angle can be a laser, LED, etc., or any combination thereof. Certain embodiments of the leak detection device can be portable. In some embodiments, the leak detection device can be powered by an internal power source (e.g., batteries). Alternatively, the leak detection device can be powered by an external power source. In some embodiments, a stethoscope may be employed as a leak detection device. In some embodiments, a leak detection device can be incorporated into a negative pressure wound therapy apparatus. For example, a monitoring device (e.g., microphone) may be connected to the apparatus via a wired or wireless interface, and leak detection may be incorporated into a pump control module of the apparatus. Leak detection can employ input/output modules and/or functions of the apparatus, such as the graphical user interface (GUI), button(s), alarm(s), etc. In some embodiments, the monitoring device can be configured to be a disposable sterile unit for single patient use. In other embodiments, the monitoring device can be configured for multi-patient use.

Methods of locating leaks are also disclosed herein. In some embodiments, a method of locating and reducing a leak comprises positioning a wound packing material in a wound cavity or on a wound surface, positioning a drape over the wound, creating a seal (e.g., substantially fluid impermeable seal) over the wound, providing negative pressure to the wound, and using a leak detection device to detect the sound waves produced by a leak, the leak detection device comprising an acoustic monitoring device. The leak detection device can be passed over the components of the negative pressure therapy system, the existence of a leak being indicated by detection of a change in sound pressure relative to background, and the location of the leak being determined by the position of the acoustic monitoring device relative to surface of the system. In some embodiments, a smart phone may be used as an acoustic monitoring device, an application for the phone being used to visually depict the sound pressure detected. Once the location of a leak is identified, it can be reduced or eliminated by any means known in the art.

In some embodiments, the leak detection device can comprise an acoustic monitoring device such as a non-directional microphone, directional microphone, unidirectional microphone, microphone array, and the like and an indicator (e.g., display) configured to visually depict the sound received by the microphone. The acoustic monitoring device can be passed over the surface of the flexible drape, the sound pressure being depicted visually on the display, the existence of a leak being indicated by observation of detected changes in sound pressure. In some embodiments, the leak detection device can comprise a visual depiction of the microphone's coverage angle, and the location of a sound source (e.g., a leak) can be found within the visual depiction of the coverage angle. In some embodiments, the coverage angle depiction can be accomplished by a laser, the location of the leak being illuminated or highlighted by the laser in combination with a leak detection device. In some embodiments, the acoustic monitoring device can be placed in the proximity to the sound source to detect the sound.

In some embodiments, the leak detection device can be configured to detect leaks associated with varying flow rates. For example, the leak detection device can be configured to detect a leak having a flow rate as low as approximately 0.25 liters/minute, which can be reflected by a change in sound pressure corresponding to, for example, approximately 5 decibels. In some embodiments, the change in sound pressure can be detected by placing the leak detection device close or in near contact with the wound. Other embodiments of the leak detection device can be configured to detect a leak with a flow rate of approximately 0.3, 0.5, 1, or 1.1 liters/minute or higher. Some embodiments can be configured to detect sound outside the audible range, such as ultrasonic waves.

DETAILED DESCRIPTION OF THE PREFERRED EMBODIMENTS

Preferred embodiments disclosed herein relate to leak detection in negative pressure wound therapy systems. Wounds include, but are not limited to, open wounds, acute wounds, chronic wounds, surgical incisions and other incisions, subacute and dehisced wounds, traumatic wounds, flaps and skin grafts, lacerations, abrasions, contusions, pressure sores, diabetic ulcers, pressure ulcers, venous ulcers, stoma, surgical wounds, trauma, burns and the like. Treatment of such wounds can be performed using negative pressure wound therapy, wherein a reduced or negative pressure can be applied to the wound to facilitate and promote healing of the wound. Leaks, which can occur at interfaces in the negative pressure wound therapy systems, may be detected through monitoring changes in sound levels, which may be represented by sound pressure level measurement, in proximity to the leaks. It will also be appreciated that leak detection apparatuses and methods as disclosed herein may be useful in a variety of pressurized systems, and are not necessarily limited to negative pressure systems or to systems directed at the treatment of wounds.

Figure 1:
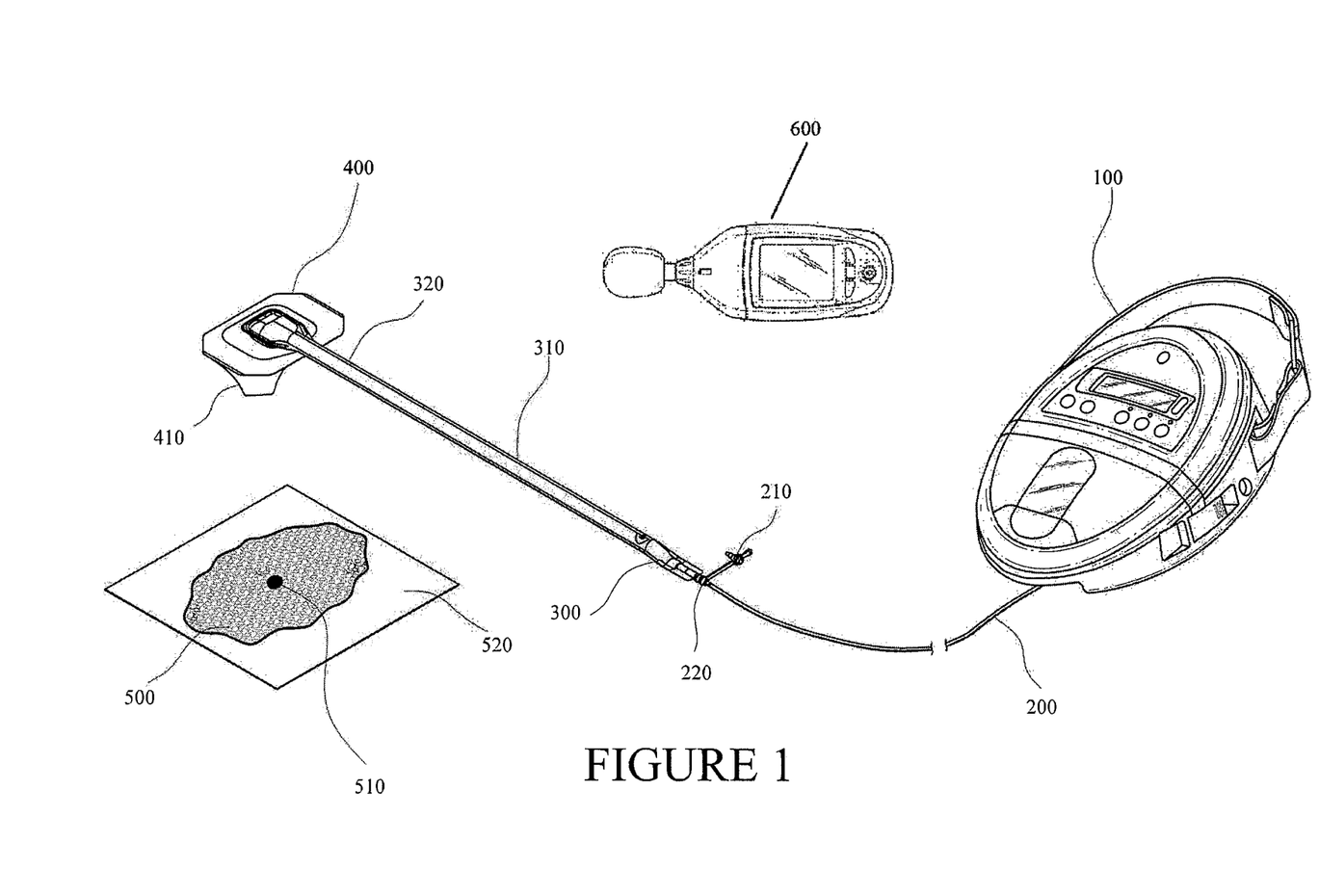
FIG. 1 illustrates a negative pressure wound therapy system being applied to a wound according to some embodiments.
Figure 2:
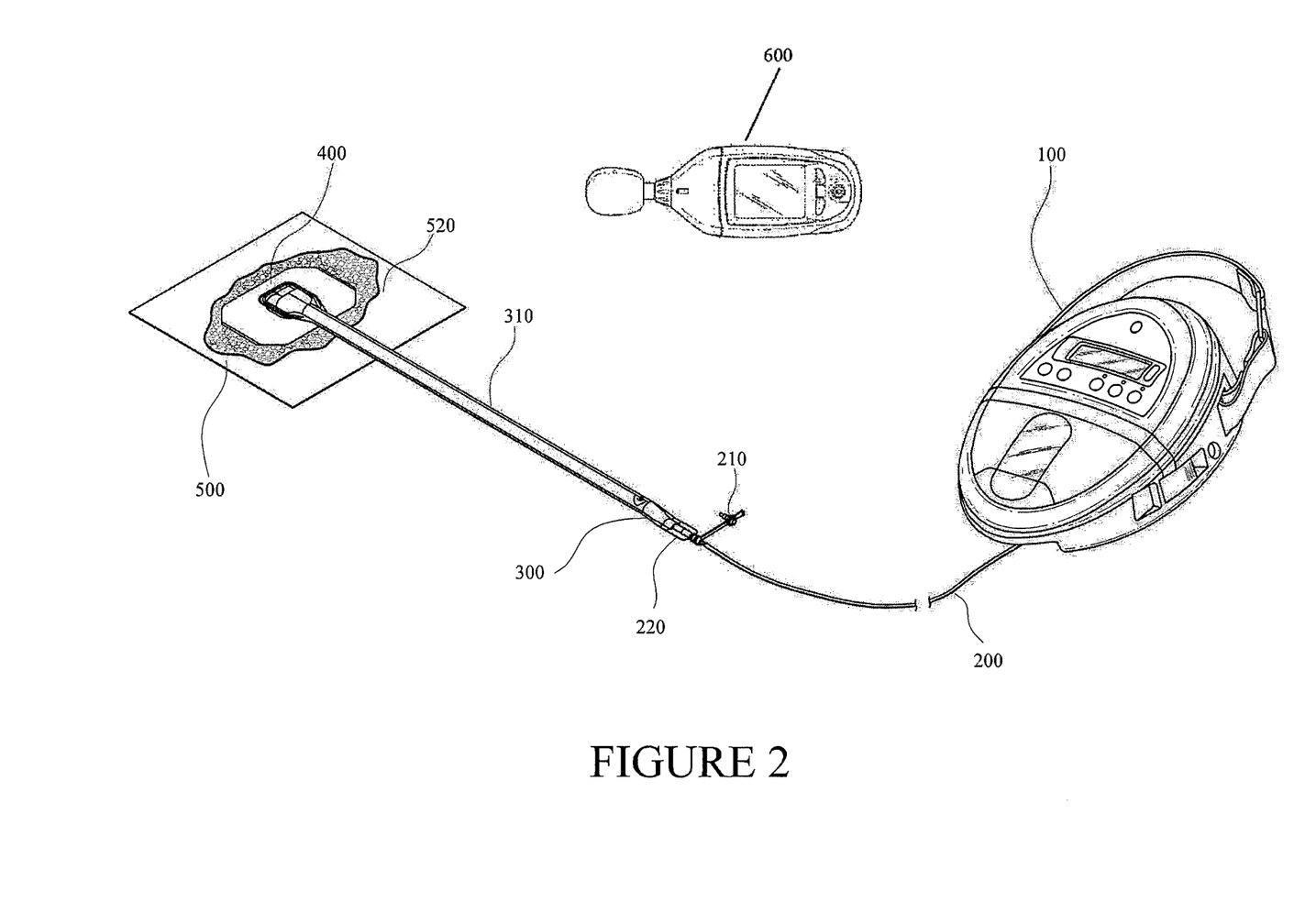
FIG. 2 illustrates the system of FIG. 1 with a flexible suction adapter having been placed over the wound.

With reference to FIGS. 1-2, a system for detecting of leaks, such as leaks in a negative pressure wound therapy system, is illustrated. In some embodiments, a flexible drape 520 that is at least partially fluid impermeable, and preferably liquid impermeable, may be laid over a suitably-prepared wound 500 and preferably onto at least part of the surrounding healthy tissue surrounding the wound 500 and sealed to the tissue of the patient. In some embodiments, wound packing material (e.g., foam, gauze, etc.) can be placed into the wound and sealed with the drape 520. The system may comprise a bridge 310 having a proximal end 300 and a distal end 320 and an applicator 400 at the distal end 320 of the bridge 310 forming a flexible suction adapter. A connector 220 is preferably disposed at the proximal end 300 of the bridge 310. A cap 210 may be provided with the system (and can in some cases, as illustrated, be attached to the connector 220). The cap 210 can be useful in preventing fluids from leaking out of the proximal end 300. The system may include a source of negative pressure such as a pump or negative pressure unit 100 capable of supplying negative pressure. In some embodiments, this pump 100 can be a RENASYS GO pump, as sold by Smith & Nephew. Other embodiments may utilize a RENASYS EZ pump, as sold by Smith & Nephew, or other pumps. The pump 100 may be connected to the connector 220 via a conduit 200. Further details of a negative pressure system such as shown in FIGS. 1 and 2 and its method of use are found in PCT Publication WO 2011/087871, entitled "Apparatuses and Methods for Negative Pressure Wound Therapy," the entirety of which is hereby incorporated by reference.

In use, the applicator 400 is placed over an aperture 510 formed in the drape 520, as is illustrated in FIG. 2. A backing layer 410 may be removed from the applicator 400 to expose an adhesive layer for sealing the applicator 400 to the drape 520. Subsequently, with the pump 100 connected via the conduit 200 to the connector 220, the pump is activated, thereby supplying negative pressure to the wound. A leak detection device 600 can be used to determine the location of leaks in the system. For example, leaks can occur in the interfaces (e.g., adhesive interfaces) between the tissue of the patient and the drape 520 and/or between the drape 520 and the applicator 400. Leaks can additionally occur at any other interface of the system, such as between the conduit 200 and the connector 220, or due to unintentional perforations of negative pressure wound therapy system components. Application of negative pressure may be applied until a desired level of healing of the wound 500 is achieved.

Figure 3:
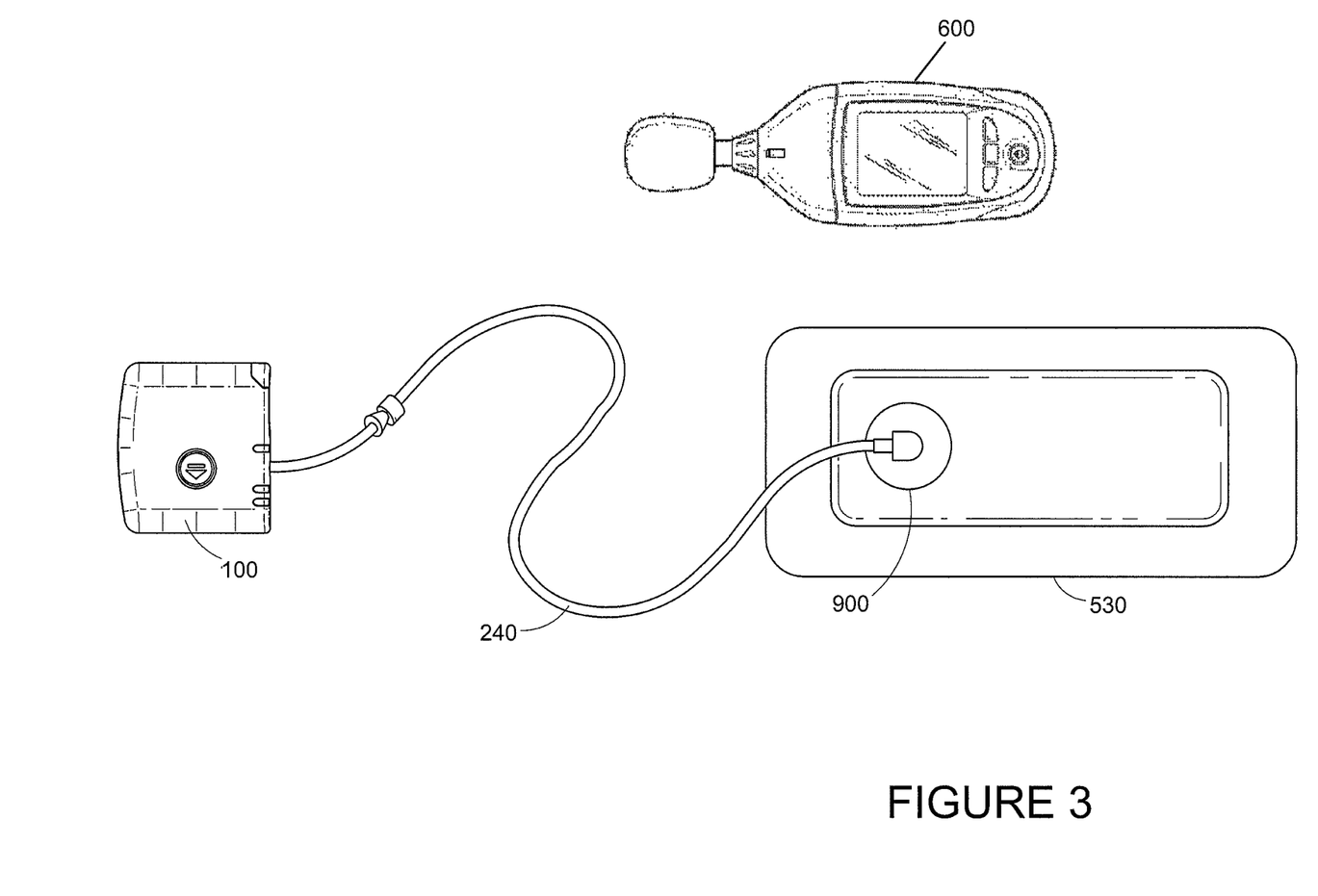
FIG. 3 illustrates another negative pressure wound therapy system in combination with a leak detection device according to some embodiments.

FIG. 3 illustrates another system for detecting leaks in a negative pressure wound therapy system according to some embodiments. As is illustrated, the negative pressure wound therapy system includes port 900 (shown as a low-profile port). The port 900 may be integrated into dressing 530. The dressing 530 can include an adhesive layer on the wound-facing surface of the drape for creating a seal with the tissue of the patient. Preferably, the seal is a substantially fluid impermeable seal. A pump or negative pressure source 100 is connected, via conduit 240, to the dressing. In some embodiments, the pump 100 can be a PICO NPWT pump, as sold by Smith & Nephew. Further details regarding the dressing and pump of FIG. 3, and its method of use, are found in U.S. application Ser. No. 13/092,042, filed Apr. 21, 2011, entitled "Wound Dressing and Method of Use," the entirety of which is hereby incorporated by reference. The leak detection device 600 can be used to determine the location of any leaks in the system, for example leaks occurring in the interface (e.g., adhesive interface) between the tissue of the patient and the dressing 530. In some embodiments, the negative pressure wound therapy system does not include a canister. For example, the dressing 530 can include be configured to absorb exudate and/or fluid removed from the wound. In some embodiments, the source of negative pressure comprises a portable, miniature pump (e.g., a battery operated miniature pump).

Figure 4:
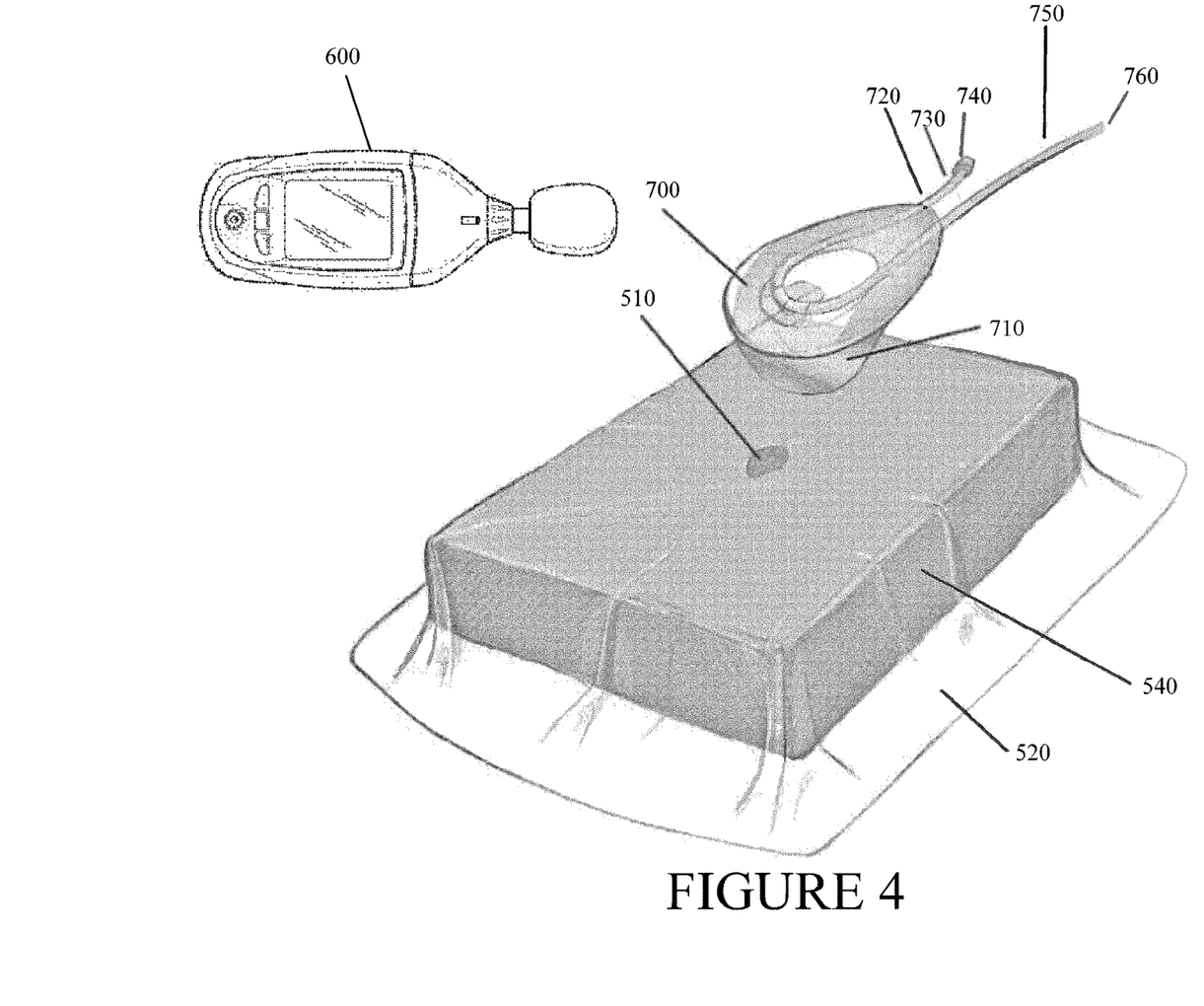
FIG. 4 illustrates another negative pressure wound therapy system in combination with a leak detection device according to some embodiments.

FIG. 4 illustrates a leak detection device 600 and a negative pressure wound treatment system according to some embodiments and illustrates the multiple surfaces which can form interfaces therein. As is shown, a suction adapter 700 comprises an integrated controlled air leak 730. The suction adapter 700 comprises at least two layers, between which the conduit 750 is sandwiched. The conduit comprises a proximal end 760 leading to a source of negative pressure and a distal end 720 extending past the loop to form the controlled air leak 730. The air leak 730 provides a constant source of air entering into the suction adapter 700 and may aid in the removal of wound exudate. For example, the air leak can provide a flow rate of approximately 0.08 L/min. Preferably, a filter 740 is placed at the end of the air leak 730 to prevent outside contaminants, such as microorganisms, dust, or other foreign matter from entering the wound area. A suitably treated wound is packed with foam 540 and is covered with a flexible drape 520 that is at least partially fluid impermeable, and preferably liquid impermeable, the drape preferably being laid onto at least part of the surrounding healthy tissue surrounding the wound 500 and sealed to the tissue of the patient. A backing layer 710 can be removed to expose an adhesive layer on the wound-facing surface of the bottom layer of the suction adapter 700 so that it may be placed over an aperture 510 in the drape 520 and sealed to the drape 520. The leak detection device 600 can be used to determine the location of uncontrolled leaks in the system, for example those occurring on the adhesive interfaces between the tissue of the patient and the drape 520 or the between the drape 520 and the suction adapter 700.

Figure 5:
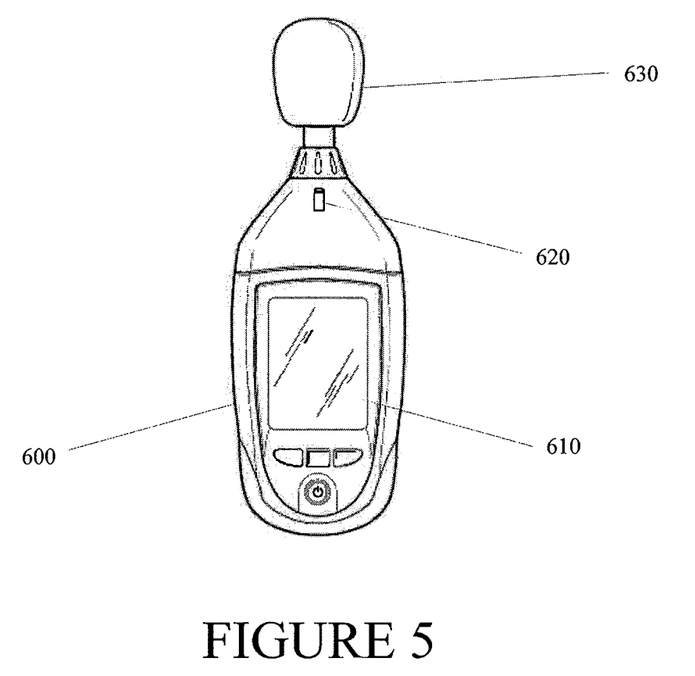
FIG. 5 illustrates a leak detection device according to some embodiments.
Figure 6:
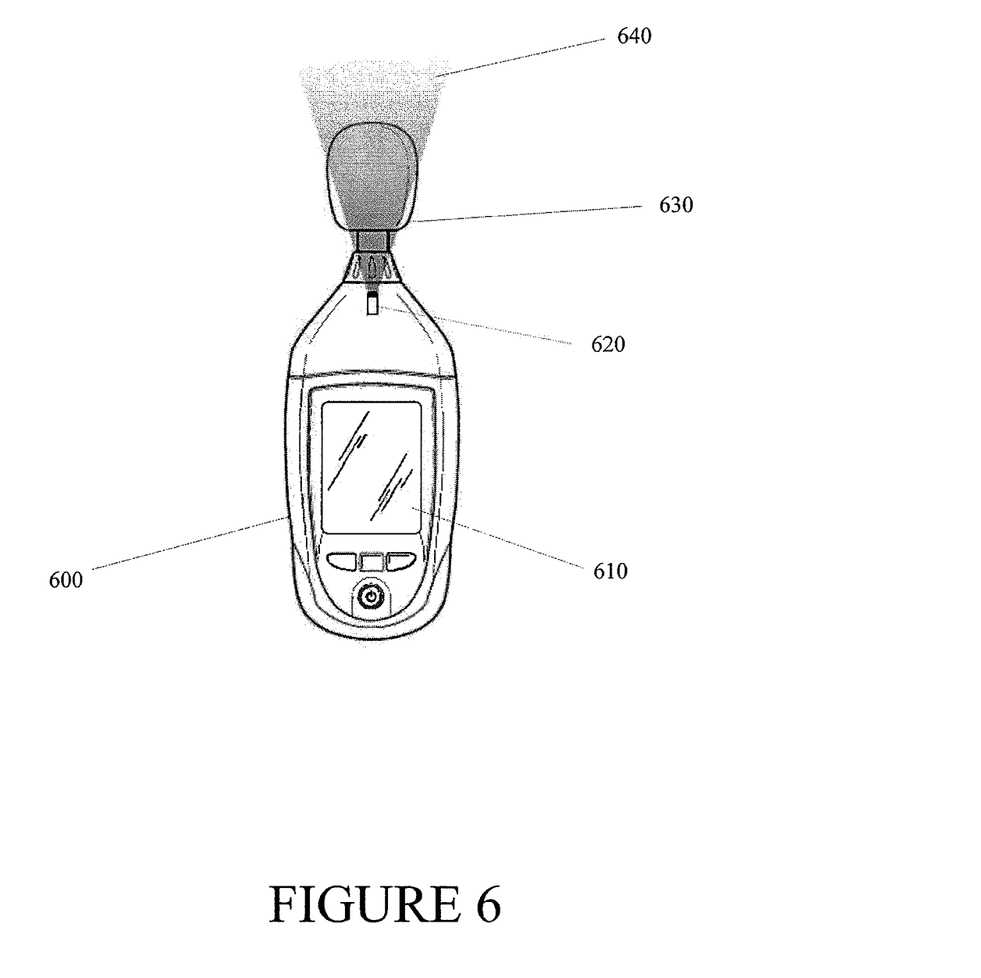
FIG. 6 illustrates the device of FIG. 5, with an activated light source depicting the coverage angle of the microphone.

FIG. 5 illustrates a leak detection device 600 according to some embodiments. The leak detection device 600 may be packaged together in a single kit with the dressing, pump and/or other components described above. Thus, the medical practitioner will have easy access to the leak detection device when the wound dressing and pump are applied to a wound. The device 600 can comprise an acoustic monitoring device 630 (e.g., a microphone), a display 610 configured to visually depict the sound waves detected by the acoustic monitoring device 630 and a light source 620 which creates a visual depiction of the coverage angle of the acoustic monitoring device 630. As is illustrated in FIG. 6, the light source 620 facilitates visual monitoring of the coverage angle 640 of the detection device 600. In some embodiments, the acoustic monitoring device 630 can be a microphone, such as a directional microphone, which can facilitate identifying the location of a leak. The microphone can have appropriate shape and size for detection of leaks. In some embodiments, the acoustic monitoring device 630 can comprise multiple microphones (e.g., narrow or small aperture microphones), which can be arranged as a microphone array to further facilitate identifying the location of a leak. Certain embodiments may employ a LED, laser, etc., or any combination thereof, as the light source 620, which is configured to visually depict the coverage angle 640. In some embodiments, the leak detection device 600 can comprise one or more processors, memories, user interfaces (e.g., buttons, knobs, touch screen interfaces, etc.), and other electronic components (not shown). In addition, the one or more processors can execute software and/or firmware.

Figure 7:
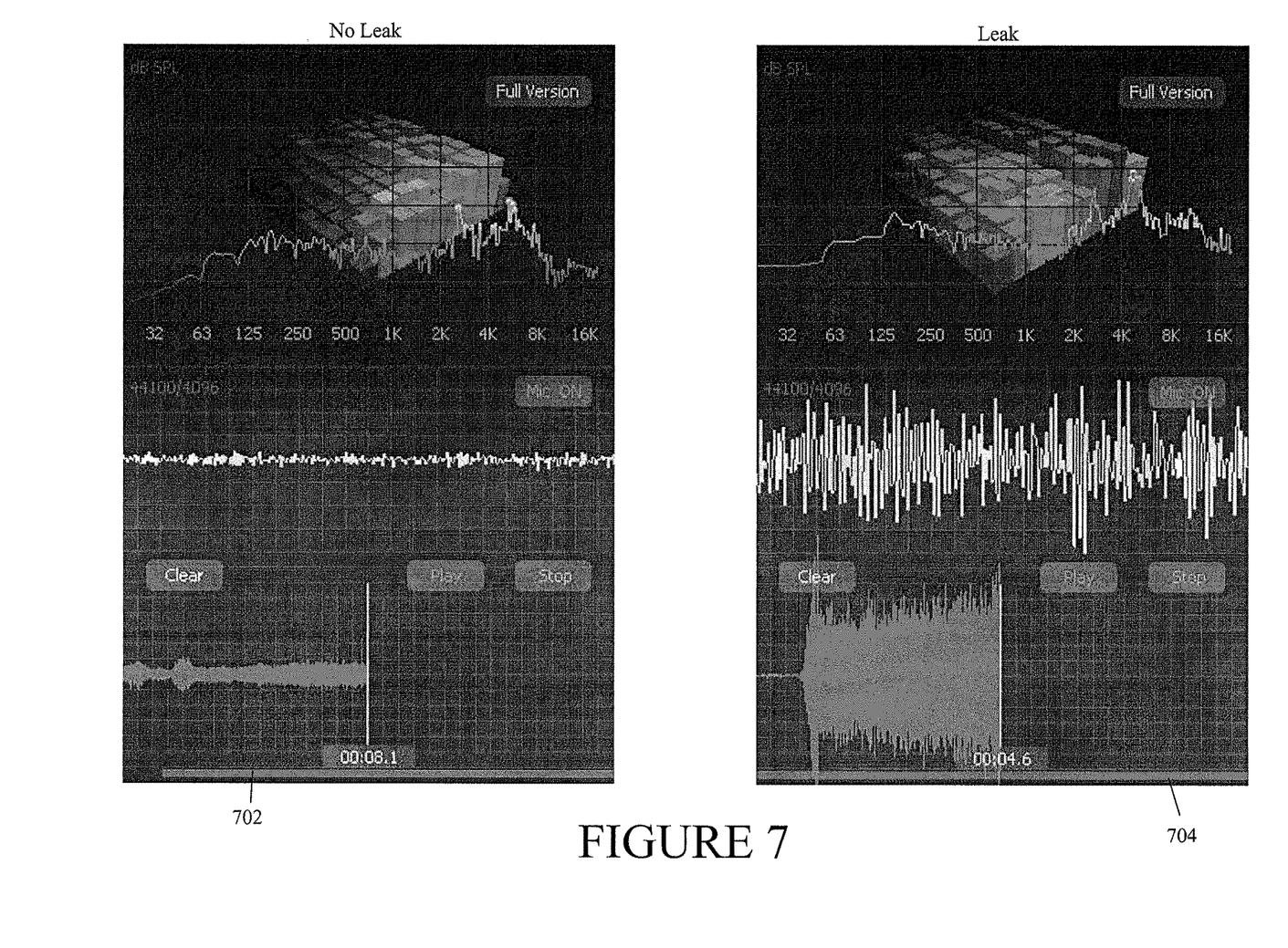
FIG. 7 illustrates a visual depiction of detected sound pressure according to some embodiments.

FIG. 7 illustrates visual depiction of monitored sound pressure, which may be represented by sound pressure level measurements, according to some embodiments. Depiction 702 illustrates monitored sound pressure levels when no leak (or low leak) is present. Depiction 704 illustrates monitored sound pressure levels when a leak is present. As is shown, sound pressure levels depicted in 704 are more pronounced (e.g., stronger) than the background or ambient noise, such as noise produced by the pump, depicted in 702. Accordingly, a user (e.g., a patient, physician, caretaker, etc.) can discern the presence of a leak detected by the detection device 600. In some embodiments, a smart phone with a microphone can be used as the leak detection device. For example, the smart phone (e.g., iPhone from Apple, Inc.) can be configured to execute a program (e.g., iAnalyzerLite application) that provides visual depiction of the detected sound pressure levels.

Figure 8:
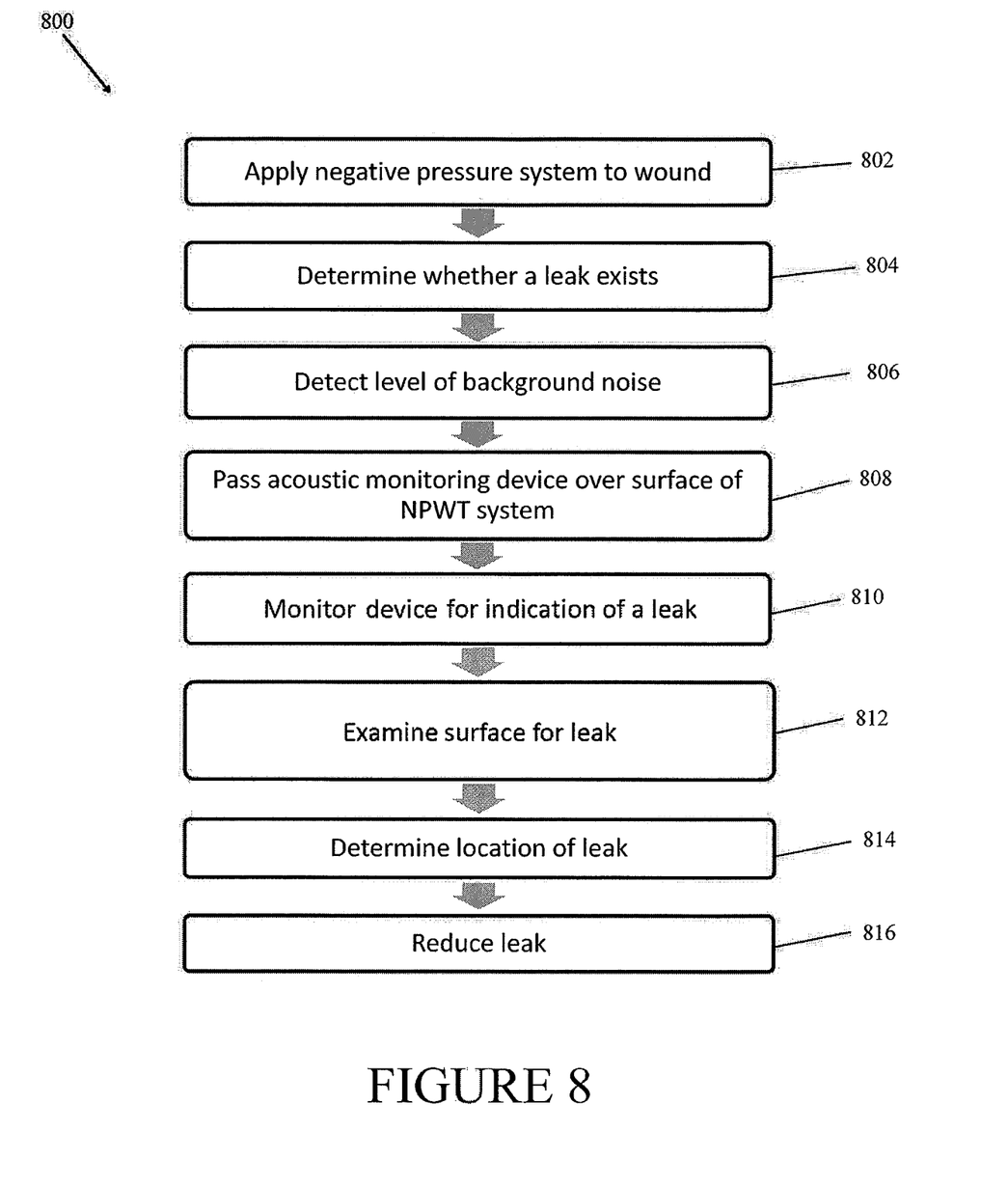
FIG. 8 is a flow chart illustrating leak detection according to some embodiments.

FIG. 8 provides an embodiment of a method 800 for locating a leak in a negative pressure wound therapy system. After applying the negative pressure system to a wound 802, the existence or nonexistence of a leak can be ascertained in 804. In some embodiments, the existence of a leak can be indicated by an alarm. For example, the alarm can be visual, auditory, or tactile, or any combination thereof. Next the background or ambient noise pressure can be determined 806 with a leak detection device. Certain embodiments can employ an acoustic monitoring device to determine a background or ambient sound pressure. For example, a negative pressure pump configured to provide −80 mmHg of reduced pressure can generate sound in the range of approximately 45 to 50 dBA. Background noise levels can be determined in some embodiments by listening to the initial sound levels with the acoustic monitoring device. For example, background noise levels can include sound resulting from the operation of the negative pressure pump. In certain embodiments the acoustic monitoring device can comprise a microphone. In some embodiments, the leak detection device may comprise a visual representation of the sound levels. In 808, the acoustic monitoring device can be passed over the surface of the system (e.g., over the surface of the drape), and can be monitored for indication of a leak 810. In some embodiments, the leak can be detected by determining a change in sound pressure levels as compared to background noise levels, which can serve as a threshold level. For example, the sound level at or near the point of the leak can be in the range of approximately 60 dBA or lower to 65 dBA or higher as compared to approximately 45 dBA or lower to 50 dBA or higher background noise levels. In some embodiments, background noise sound pressure level can be measured over a period of time, such as 30 seconds, 45 seconds, 1 minute, or the like, and an average, median, etc., of detected sound pressure levels over the period of time can be computed. For example, background noise sound pressure can be measured every 30 seconds over a 2 minute interval, and the four measurements can be averaged. This may help to determine accurate background sound pressure. In other embodiments, any other suitable threshold can be used, such as a threshold defined and/or selected by the user.

In some embodiments, sound pressure levels can be measured over a period of time, such as 30 seconds, 45 seconds, 1 minute, or the like, and an average, median, etc., of detected sound pressure levels over the period of time can be computed. For example, sound pressure levels can be measured every 30 seconds over a 2 minute interval, and the four measurements can be averaged. This may help to determine accurate sound pressure levels by removing noise, such as spurious noise, from the measured sound pressure. In some embodiments, filtering (e.g., low-pass filtering) or other suitable signal processing techniques can be performed alternatively or in addition to calculation of average, median, etc. of detected sound pressure levels. Presence and/or location(s) of leak(s) can be detected by passing the leak detection device 600 over the surface of the negative pressure wound therapy system without manipulating or otherwise disturbing any of the components of the system. For example, it may be unnecessary to apply force to (e.g., press down on) the drape in order to detect presence and/or location(s) of leak(s).

Certain embodiments may employ an alarm to indicate the presence of a leak. The alarm can be audible, visual, tactile, or any combination thereof. Some embodiments may change the visual representation of the sound pressure levels to indicate the sound level of a leak. The location of the leak can be determined in 812 and 814. In some embodiments, this can be accomplished by examining the surface of the system near to the acoustic monitoring device. Other embodiments can locate the leak by means of a visualization of the coverage angle of a microphone in the device. For example, certain embodiments can employ a laser to visualize the microphone's aperture, and the leak can be located using the beam of the laser. Other embodiments can employ a LED to visualize or highlight the coverage angle, and the leak can be illuminated or highlighted by the LED. In some embodiments, the body or assembly of the directional microphone can serve as a pointer, and the leak can be located in the proximity of the microphone. Once the location is determined the leak may be reduced and/or repaired in 816. For example, the leak can be reduced and/or repaired by resealing the wound cover. As another example, the leak can be reduced and/or repaired by applying a applying a sealing agent, such as an adhesive sealing agent.

Figure 9:
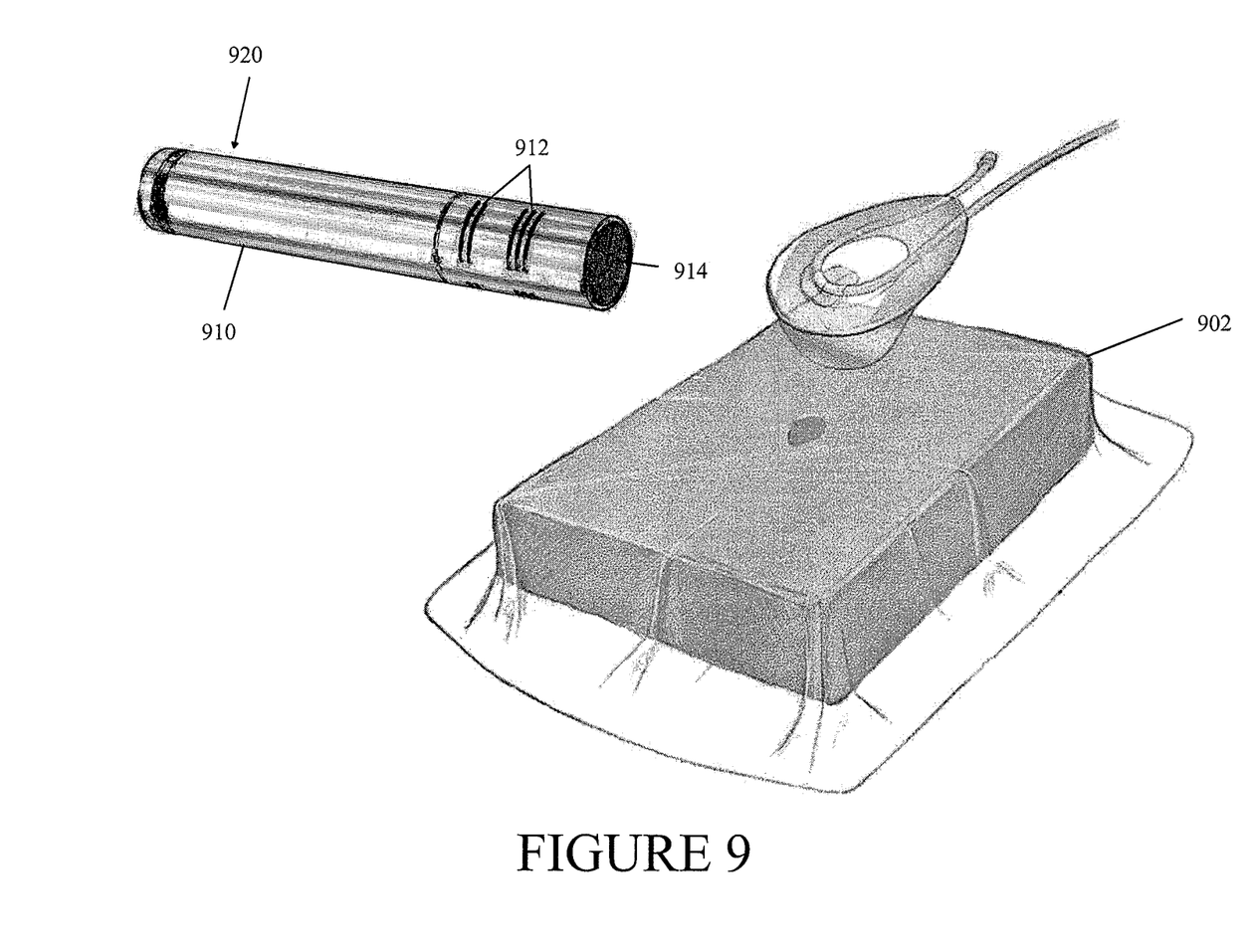
FIG. 9 illustrates the negative pressure wound therapy system of FIG. 4 in combination with another leak detection device according to some embodiments.

FIG. 9 illustrates the negative pressure wound therapy system of FIG. 4 in combination with another leak detection device 920 according to some embodiments. In some embodiments, the leak detection device 920 comprises a directional microphone 910 having a primary sound inlet 914 and sound pressure cancellation slits 912. The directional microphone 910 can be used to examine the negative pressure wound therapy system 902 for a leak. The sound pressure cancellation slits 912 can be configured to increase the directionality of the microphone 910, such as by using sound wave cancellation to eliminate at least some of the off-axis sound. In some embodiments, the increased directionality of the microphone 910 can be used to determine the location of a leak in the negative pressure wound therapy system 902. Although FIG. 9 illustrates the leak detection device 920 in combination with the negative pressure wound therapy system of FIG. 4, the leak detection device 920 can be used with any negative pressure wound therapy system illustrated or disclosed herein or any other negative pressure wound therapy system. Further, the leak detection device 920 can be used in place of or together with any other leak detection device illustrated or disclosed herein or any other leak detection device.

Figure 10:
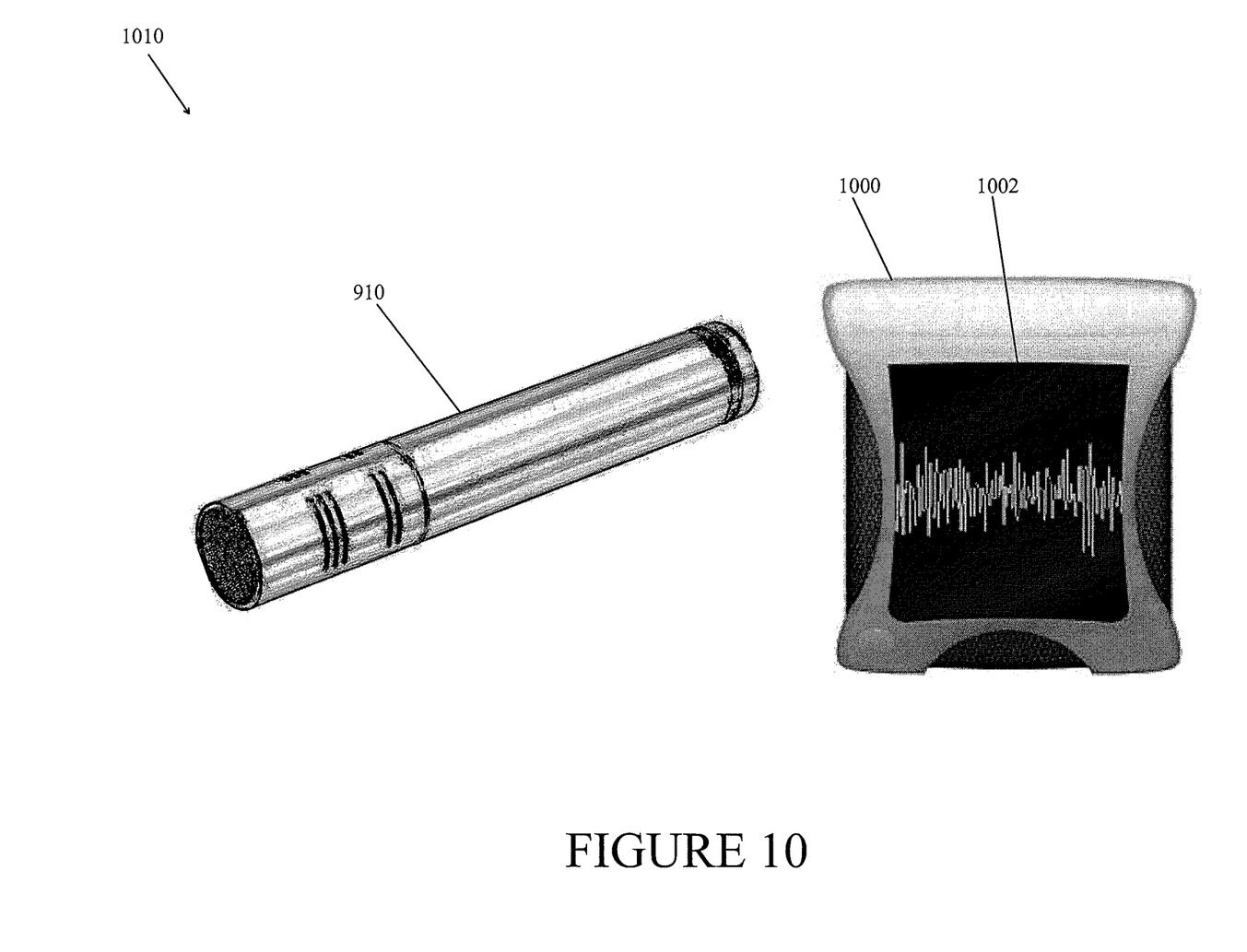
FIG. 10 illustrates another leak detection device according to some embodiments.

FIG. 10 illustrates another leak detection device 1010 according to some embodiments. As is illustrated, the leak detection device 1010 can comprise an acoustic monitoring device (e.g., a directional microphone) 910 and an indicator device 1000. The indicator device can be configured to comprise a display 1002 configured to provide a visualization of the detected sound waves. The acoustic monitoring device 910 can be connected to the indicator device 1000 by a wireless or wired connection, as is known in the art. For example, the wireless connection can include Bluetooth, WiFi, IrDA, etc. or any combination thereof. In some embodiments, the leak detection device 1010 can be incorporated into a negative pressure wound therapy apparatus and use a GUI of the apparatus. For example, the monitoring device 910 may be connected to the apparatus via a wired or wireless interface and leak detection may be incorporated into a pump control module of the apparatus. In some embodiments, the monitoring device 910 can be configured to be a disposable sterile unit for single patient use. In other embodiments, the monitoring device 910 can be configured for multi-patient use.

Figure 11:
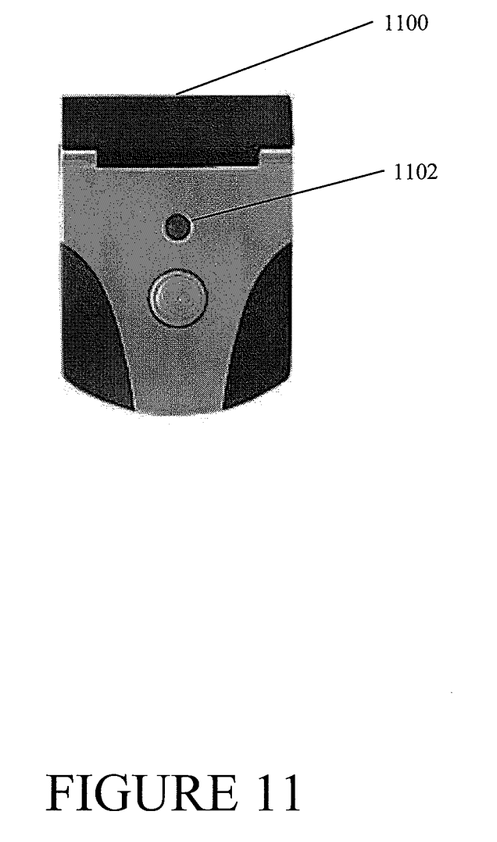
FIG. 11 illustrates yet another leak detection device according to some embodiments.

FIG. 11 illustrates yet another leak detection device 1100 according to some embodiments. The leak detection device 1100 can comprise an indicator 1102, such as an LED. The leak detection device 1100 can be configured to activate the indicator when a leak is detected. In some embodiments, the indicator can be configured to remain active when the leak detection device remains the proximity of the leak. In some embodiments, the leak detection device 1100 can provide additional indication or indications, such as a speaker configured to produce an alarm to indicate that a leak is present.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. Further, actual steps take in processes disclosed herein may differ from those illustrated and described. Depending on the embodiment, certain steps may be removed, others may be added. Various components illustrated in the figures and/or described herein may be implemented as software and/or firmware on a processor, ASIC, FPGA, or dedicated hardware. All possible combinations and subcombinations are intended to fall within the scope of this disclosure. Many of the embodiments described above include similar components, and as such, these similar components can be interchanged in different embodiments.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A system for monitoring provision of negative pressure wound therapy, comprising:

a directional microphone configured to be positioned at a first location proximate a dressing covering a wound and configured to be connected, via a fluid flow path, to a negative pressure source configured to provide a negative pressure wound therapy to the wound, the microphone configured to sense at the first location a first sound pressure wave propagating from the dressing, the microphone further configured to generate a first signal based on the first sound pressure wave propagating from the dressing; and a controller configured to receive from the microphone and process the first signal to determine a first status of provision of the negative pressure wound therapy at the first location and provide a first indication of the first status at the first location.

2. The system according to claim 1, wherein the controller is part of a mobile device.

3. The system according to claim 2, wherein the mobile device includes the microphone.

4. The system according to claim 1, wherein the first indication comprises an alarm.

5. The system according to claim 1, wherein the microphone is configured to be positioned at a second location proximate the dressing to sense at the second location a second sound pressure wave propagating from the dressing, the microphone further configured to generate a second signal based on the second sound pressure wave propagating from the dressing, and wherein the controller is further configured to receive from the microphone and process the second signal to determine a third status of provision of the negative pressure wound therapy at the second location and provide a third indication of the third status.

6. The system according to claim 1, wherein the microphone is configured to measure a plurality of sound pressure waves over a period of time, and wherein the controller is further configured to determine a representative sound pressure based on the plurality of measured sound pressure waves.

7. The system according to claim 6, wherein the controller is configured to determine the representative sound pressure based on an average of the plurality of measured sound pressures.

8. The system according to claim 6, wherein the controller is configured to determine the representative sound pressure based on low-pass filtering the plurality of measured sound pressures.

9. The system according to claim 1, further comprising an electronic display coupled to the controller, the electronic display configured to provide information relating to the first sound pressure wave.

10. The system according to claim 1, wherein the controller is further configured to generate a graphical indicator of the first sound pressure wave at the first location.

* * * * *